United States Patent

Welstead, Jr. et al.

[11] 4,021,552
[45] May 3, 1977

[54] 10-[ω-(BENZOYLPIPERIDINYL)ALKYL]-PHENOTHIAZINES

[75] Inventors: William J. Welstead, Jr.; Robert F. Boswell, Jr., both of Richmond, Va.

[73] Assignee: A. H. Robins Company, Incorporated, Richmond, Va.

[22] Filed: Apr. 20, 1976

[21] Appl. No.: 678,575

Related U.S. Application Data

[63] Continuation of Ser. No. 591,216, June 27, 1975, abandoned.

[52] U.S. Cl. .......................... 424/247; 260/243 A; 260/293.8
[51] Int. Cl.² ............... C07D 417/06; A61K 27/00
[58] Field of Search ............... 260/243 A, 293.8; 424/247

[56] References Cited

UNITED STATES PATENTS

| 3,225,037 | 12/1965 | Zenitz et al. ............... 260/243 A |
| 3,637,660 | 1/1972 | Eriksoo et al. ............... 260/243 A |

FOREIGN PATENTS OR APPLICATIONS

| 863,243 | 3/1961 | United Kingdom ............ 260/243 A |

OTHER PUBLICATIONS

Schenker–Herbst, Drug Research, vol. 5, pp. 288 to 289 and 419 to 426, Birkhauser Verlag Basel und Stuttgart, (1963).
Chemical Abstracts, vol. 72, Abst. No. 100535h, (1970), (Abst. of German Offen. 1,930,818).

*Primary Examiner*—John D. Randolph

[57] ABSTRACT

10-[ω-(Benzoylpiperidinyl)alkyl]phenothiazines having the formula

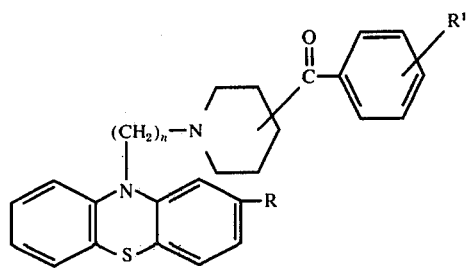

wherein R is hydrogen, chloro, bromo, trifluoromethyl, lower alkoxy, acetyl, sulfamoyl, or dimethylsulfamoyl, $R^1$ is hydrogen, chloro, bromo, fluoro, trifluoromethyl, lower alkyl or lower alkoxy and n is 2, 3 or 4 are disclosed. Methods for the preparation of the compounds are described. The compounds possess tranquilizing activity and are useful as tranquilizing agents in mammals.

22 Claims, No Drawings

10-[ω-(BENZOYLPIPERIDINYL)ALKYL]PHENOTHIAZINES

This is a continuation, division, of application Ser. No. 591,216, filed June 27, 1975, now abandoned.

The present invention concerns phenothiazines and is more particularly concerned with 10-[ω-(benzoylpiperidinyl) alkyl]phenothiazines, compositions containing the same as activve ingredients and the methods of making and using them.

The novel compounds of the present invention correspond to the general Formula I:

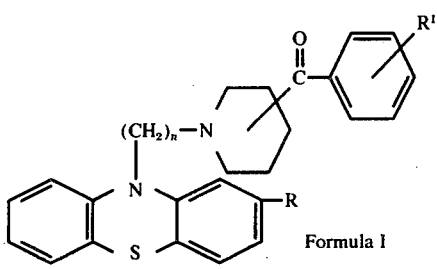

Formula I wherein;

R represents hydrogen, chloro, bromo, trifluoromethyl, lower alkoxy, acetyl, sulfamoyl, or dimethylsulfamoyl, $R^1$ represents hydrogen, chloro, bromo, fluoro, trifluoromethyl, lower alkyl or lower alkoxy, n is a positive integer from 2–4 inclusive, and non-toxic pharmaceutically acceptable acid addition salts thereof.

The present invention contemplates various embodiments as can be seen from Formula I and the respective values assigned to the symbols R, $R^1$ and n.

In one embodiment of the present invention the value of n can be 2 through 4 inclusive and R is hydrogen, while in another embodiment n can have the value of 3 or 4 and R is chloro or bromo.

Another embodiment of the invention contemplates compounds wherein n is 3, R is chloro, bromo, or fluoro, and the benzoyl moiety is attached to the 3 or 4 position of the piperidine nucleus.

A preferred embodiment of the present invention is represented by compounds wherein n is 3, R is chloro or bromo, $R^1$ is fluoro, and the benzoyl moiety is attached to the 4-position of the piperidine ring.

The compounds of the invention having the foregoing Formula I are generally characterized by important pharmacological activity and exhibit tranquilizing activity and are particularly useful in inducing an antianxiety effect in a living animal body.

The tranquilizing activity of the novel compounds of the present invention was demonstrated by their ability to block the lethal effects of d-amphetamine in aggregated mice when tested according to a modified procedure of Burn and Hobbs, Arch. Intern. Pharmacodyn. 113: 290 (1958). For example, when 2-chloro-10-[3-(4-p-fluorobenzoylpiperidinyl)propyl]phenothiazine was administered I.P. in rats the compound had an $ED_{50}$ of 0.72 mg/kg after 16 hours, indicating the compound had effective and long lasting tranquilizing properties. The $ED_{50}$ values of the foregoing compound and additional compounds are summarized in Table 1.

Table 1

| Example No. | Effects of different pretreatment time intervals on d-amphetamine lethality in mice Protective $ED_{50}$ (95% confidence limits) mg/kg IP | | | |
|---|---|---|---|---|
| | 1 hr. | 4 hrs. | 8 hrs. | 16 hrs. |
| 7 | 0.17(.1–14) | 0.53(.2–1.1) | 0.19(.1–.5) | 0.72(.4–1.3) |
| 6 | 0.14(.06–.3) | 0.10(.05–.22) | 0.06(.03–.13) | 0.76(.6–1.1) |
| 1 | 0.94(.4–1.9) | 0.35(.1–1.2) | 1.27(.7–2.1) | 12.1(8–18) |
| 4 | 1.44(.6–3.3) | 3.5(1.1–10.8) | 1.4(.8–2.2) | 1.89(1.2–2.8) |

The acute toxicities ($LD_{50}$'s) of the compounds of Examples 1, 4, 6 and 7 were determined in mice and are summarized in Table II.

Table II,

| Example No. | 72 hour $LD_{50}$'s in Mice $LD_{50}$ (95% Confidence Limits) mg/kg IP |
|---|---|
| 7 | 248 (211–290) |
| 6 | 287 (227–361) |
| 1 | 330 (268–405) |
| 4 | 317 (251–399) |

It is, therefore, an object of the present invention to provide novel compounds and compositions possessing valuable pharmacological properties; that is, tranquilizing activity, and a method for their preparation. Another object is to provide a novel method for the treatment of living animal, and especially mammalian bodies, for purposes of relieving anxiety therein. Still another object is to provide compositions which possess beneficial tranquilizing activity and have minimum side effects. Additional objects will be apparent to one skilled in the art and still other objects will become apparent hereinafter.

In the definition of the symbols in the foregoing Formula I and where they appear elsewhere throughout the specification and the appended claims the terms have the following significance.

The term "lower-alkyl" as used in the specification and claims includes straight and branched chain radicals of up to eight carbon atoms inclusive and is exemplified by such groups as methyl, ethyl, propyl, isopropyl, butyl, isobutyl, tertiary butyl, amyl, isoamyl, hexyl, heptyl and octyl.

The term "lower-alkoxy" has the formula -O-lower-alkyl.

The compounds of the invention are preferably employed in the form of non-toxic pharmaceutically acceptable acid addition salts. Such salts have improved water solubility over the free base. Although the non-toxic salts are preferred, any salt may be prepared for use as a chemical intermediate, as in the preparation of another acid addition salt suitable for administration to an animal body for the desired physiological effect tthereof. Appropriate pharmaceutically acceptable acid addition salts are those derived from inorganic acids such as hydrochloric, hydrobromic, sulfuric and phosphoric, and organic acids such as acetic, citric, lactic, maleic, oxalic, fumaric and tartaric. The preferred addition salts are the hydrochloride, maleate, citrate, fumarate and oxalate. The acid addition salts of the product compounds are conventionally prepared by reaction of the basic compounds with the acid, either or both of which may be in the form of ether, alcohol or acetone solutions.

The starting materials used in preparing the novel compounds of the present invention are phenothiazine and 2-substituted phenothiazines which are commercially available or which can be prepared by known procedures described in the chemical literature and 1-(ω-haloalkyl)-4-(2 or 3)-benzoylpiperidines. The latter compounds are prepared by reacting 4-(2 or 3)-benzoylpiperidines with ω-haloalkanols in a lower alkanol solvent such as n-butanol with an acid acceptor to give 1-(ω-hydroxyalkyl)-4-(2 or 3)-benzoylpiperidines which on reaction with a reagent such as thionyl chloride gives the 1-(ω-haloalkyl)-4-(2 or 3)-benzoylpiperidine.

The 4-(2 or 3)-benzoylpiperidines are known compounds or they can be prepared according to methods disclosed in U.S. Pat. No. 3,576,810.

The compounds of the present invention are prepared by reacting a 1-(ω-haloalkyl)-4-(2 or 3)-benzoylpiperidine of the formula

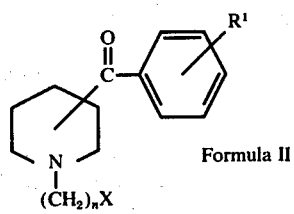

Formula II wherein $R^1$ and $n$ are as described above and X is chloro, bromo or iodo, but preferably chloro, with a phenothiazine of the formula

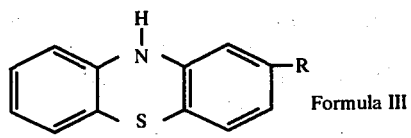

Formula III wherein R is as described above. The reaction is preferably carried out in the presence of a suitable solvent as, for example, benzene, toluene, xylene and the like and in the presence of an acid acceptor such as a strong inorganic base. The reaction is preferably carried out at an elevated temperature as, for example, reflux temperature. In a variation of the foregoing procedure the phenothiazine is metallated in a suitable solvent such as benzene, toluene, dimethylformamide, and the like, using a conventional metallating agent as, for example, sodium hydride or n-butyllithium and at an elevated temperature, e.g., 80°–110° C. and the 1-(ω-haloalkyl)-4-(2 or 3)-benzoylpiperidine is reacted with the metallated phenothiazine.

Alternately, the compounds of the invention may be prepared by the following method.

A 10-(ω-haloalkyl)phenothiazine of the formula

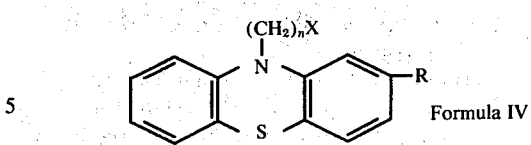

Formula IV wherein R and $n$ are as defined and X is chloro, bromo or iodo, but preferably chloro, is reacted with a benzoylpiperidine of the formula

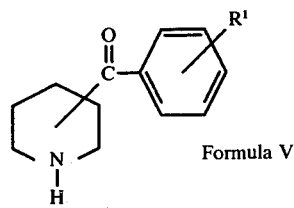

Formula V wherein $R^1$ is as described above, in a suitable aprotic solvent, e.g., benzene, xylene, toluene and the like, preferably at elevated temperature, e.g., 80°–130° C. in the presence of an acid acceptor such as a strong inorganic base.

The compounds prepared by the foregoing procedures are isolated from the reaction mixture by utilizing suitable techniques as, for example, distillation, chromatography, crystallization or by conversion to a suitable acid addition salt.

PREPARATION 1

4-(p-Fluorobenzoyl)-1-(3-hydroxypropyl)piperidine.

A mixture of 24.3 g. (0.1 mole) of 4-(p-fluorobenzoyl)-piperidine hydrochloride, 12.5 g. (0.125 mole) of 3-chloropropanol and 42.0 g. (0.5 mole) of sodium bicarbonate in 500 ml. of n-butanol was stirred at reflux for 15 hours. An additional 3.0 g. (0.025 mole) of 3-chloropropanol was added after thin layer chromatography showed incomplete reaction and the reaction was continued for 3 hours. The cooled reaction mixture was filtered, the filtrate concentrated at reduced pressure and the residual oil crystallized by trituration in isopropyl ether. The tan solid weighed 23 g. (87%) and melted at 107°–109° C. Recrystallization from benzene-isooctane gave 17.7 g. of material melting at 111°–112° C.

PREPARATION 2

4-(p-Fluorobenzoyl)-1-(3-chloropropyl)piperidine.

Thionyl chloride (38.7 g., 0.376 mole) was added dropwise to a stirring solution of 4-(p-fluorobenzoyl)-1-(3-hydroxypropyl) piperidine (43.1 g., 0.163 mole) in 400 ml. chloroform at room temperature. After the addition was complete the reaction mixture was stirred at room temperature an additional 16 hours. The mixture was then chilled and 125 ml. 6N sodium hydroxide solution was added dropwise. The chloroform solution was separated, washed with water, and dried over magnesium sulfate. Removal of the solvent gave 42.7 g. crude product (92% yield) with crystallized on cooling. Recrystallization from isooctane gave 25.3 g. pure product, m.p. 66.5°–68.5° C.

Analysis: Calculated for $C_{15}H_{19}NOFCl$: C, 63.49; H, 6.75; N, 4.94; Found: C, 63.49; H, 6.86; N, 4.81.

PREPARATION 3

2-Bromo-10-(3-chloropropyl)phenothiazine.

A solution of 2-bromophenothiazine (41.72 g., 0.05 mole) in 200 ml. of dry toluene was added to a stirred solution of 9.6 g. (0.15 mole) of n-butyllithium in 100 ml. of dry toluene. The stirred solution was warmed for about 2.0 hours at 45°–50° C. and then 31.5 g. (0.20 mole) of bromopropylchloride in 50 ml. of dry toluene was added. The mixture was refluxed for 15 hours. The cooled reaction mixture was washed with water, dried over sodium sulfate and the dried solution concentrated at reduced pressure. The residual oil was distilled to give the product, 2-bromo-10-(3-chloropropyl)phenothiazine.

EXAMPLE 1

10-[3-(4-p-Fluorobenzoylpiperidinyl)propyl]phenothiazine Fumarate Hydrate (1:4)

A mixture of phenothiazine (4.9 g., 0.025 mole), 1-(3-chloropropyl)-4-(p-fluorobenzoyl)piperidine (7.5 g., 0.0265 mole) and crushed potassium hydroxide pellets (8.4 g., 0.15 mole) was stirred in 200 ml. dry toluene at reflux for 20 hours. The cooled reaction mixture was filtered and the filtrate concentrated at reduced pressure. The residual oil was shown to be a mixture of product and reactants by thin layer chromatography analysis. Partial purification was achieved by dissolving the oil in ether and treating with ethereal hydrogen chloride solution to form the hydrochloride salt. The salt would not recrystallize, however, and was converted to the free base. The free base (4.5 g., 40.5% yield) was treated with one equivalent of fumaric acid to form the fumarate salt. Recrystallization from methanol-isopropyl ether yielded 4.7 g. tan solid, m.p. 190°–192° C.

Analysis: Calculated for $C_{29}H_{39}N_2OFS \cdot C_4H_4O_4 \cdot 1/4 H_2O$: C, 65.65; H, 5.60; N, 4.94; Found C, 65.82; H, 5.60; N, 4.93.

EXAMPLE 2

When, in the procedure of Example 1, 1-(3-chloropropyl)-4-(p-fluorobenzoyl)piperidine is replaced by an equal molar amount of:
1-(3-chloropropyl)-4-(p-chlorobenzoyl)piperidine,
1-(3-chloropropyl)-4-(p-bromobenzoyl)piperidine,
1-(3-chloropropyl)-4-(m-fluorobenzoyl)piperidine,
1-(3-chloropropyl)-4-(m-trifluoromethylbenzoyl)piperidine, there are obtained,
10-[3-(p-chlorobenzoylpiperidinyl)propyl]phenothiazine,
10-[3-(p-bromobenzoylpiperidinyl)propyl]phenothiazine,
10-[3-(m-fluorobenzoylpiperidinyl)propyl]phenothiazine,
10-[3-(m-trifluoromethylbenzoylpiperidinyl)propyl]phenothiazine, respectively.

EXAMPLE 3

When, in the procedure of Example 1, phenothiazine is replaced by an equimolar amount of:
2-sulfamoylphenothiazine, or
2-dimethylsulfamoylphenothiazine, there are obtained,
2-sulfamoyl-10-[3-(4-p-fluorobenzoylpiperidinyl)propyl]phenothiazine, and
2-dimethylsulfamoyl-10-[3-(4-p-fluorobenzoylpiperidinyl)propyl]phenothiazine.

EXAMPLE 4

2-Trifluoromethyl-10-[3-(4-p-fluorobenzoylpiperidinyl) propyl]phenothiazine Fumarate.

A mixture of 2-trifluoromethylphenothiazine (8.6 g., 0.032 mole), 1(3-chloropropyl-4-(p-fluorobenzoyl)-piperidine (10.0 g., 0.035 mole), and crushed potassium hydroxide pellets (11.2 g., 0.2 mole) was stirred in 300 ml. dry toluene at reflux for 20 hours. The cooled reaction mixture was filtered, the filtrate washed with water, dried over magnesium sulfate, and concentrated to give 14.2 g. crude product (88% yield). The crude product was treated with excess fumaric acid in methanolisopropyl ether to give 20.5 g. fumarate salt. Recrystallization from isopropanol-isopropyl ether gave 12.2 g. fumarate salt, m.p. 158.5°–161° C.

Analysis: Calculated for $C_{32}H_{30}N_2O_5SF_4$: C, 60.94; H, 4.80; N, 4.44; Found: C, 60.77; H, 4.88; N, 4.37.

EXAMPLE 5

When, in the procedure of Example 4, 1-(3-chloropropyl-4-(p-fluorobenzoyl)piperidine is replaced by an equal molar amount of:
1-(2-chloroethyl-4-(p-fluorobenzoyl)piperidine,
1(2-chloroethyl)-4-(p-chlorobenzoyl)piperidine,
1-(2-chloroethyl)-4-(m-trifluoromethylbenzoyl)piperidine,
1-(4-chlorobutyl)-4-(p-fluorobenzoyl)piperidine, and
1-(4-chlorobutyl)-4-(p-bromobenzoyl)piperidine,
there are obtained,
2-trifluoromethyl-10-[2-(p-fluorobenzoylpiperidinyl)ethyl] phenothiazine,
2-trifluoromethyl-10-[2-(p-chlorobenzoylpiperidinyl)ethyl] phenothiazine,
2-trifluoromethyl-10-[2-(m-trifluoromethylbenzoylpiperidinyl) ethyl]phenothiazine,
2-trifluoromethyl-10-[4-(p-fluorobenzoylpiperidinyl)butyl] phenothiazine, and
2-trifluoromethyl-10-[4-(p-bromobenzoylpiperidinyl)butyl] phenothiazine, respectively.

EXAMPLE 6

2-Acetyl-10-[3-(4-p-fluorobenzoylpiperidiny)propyl] phenothiazine Difumarate Sesquihydrate.

A mixture of 2-acetylphenothiazine (7.7 g., 0.032 mole), 1-(3-chloropropyl)-4-(p-fluorobenzoyl)piperidine (10.0 g., 0.0353 mole) and crushed potassium hydroxide pellets (14.0 g., 0.25 mole) was stirred in 300 ml. dry toluene at reflux for 24 hours. Thin layer chromatography showed incomplete reaction. An additional 10.0 g. (0.0353 mole) of 1-(3-chloropropyl)-4-(p-fluorobenzoyl)piperidine in 75 ml. dry toluene was added to the reaction mixture and reflux continued for an additional 24 hours. The cooled reaction mixture was washed with water, dried over magnesium sulfate and concentrated to give 23.2 g. crude product. Chromatography on 400 g. magnesium silicate gave 6 g. of impure product. Impurities were removed by molecular distillation, leaving the product as the residue. The residue weighed 4.0 g. (24.5% yield). The free base was treated with two equivalents of fumaric acid in methanol. The methanol was evaporated and the solid residue recrystallized from acetone-petroleum ether (30°–60° C.); m.p. 146°–149° C.

Analysis: Calculated for $C_{74}H_{80}N_4O_{23}S_2F_2$: C,59,43; H, 5.39; N, 3.75; Found: C, 59.57; H, 5.06; H, 3.39.

EXAMPLE 7

2-Chloro10-[3-(4-p-fluorobenzoylpiperidinyl)propyl] phenothiazine Hydrochloride Hydrate (1:4).

A mixture of 2-chlorophenothiazine (9.4 g., 0.04 mole), 4-(p-fluorobenzoyl)-1-(3-chloropropyl)-piperidine (12.0 g., 0.0425 mole) and crushed potassium hydroxide pellets (14.0 g., 0.25 mole) in 300 ml. dry toluene was stirred and refluxed for 36 hours. After cooling, the toluene solution was decanted away from the inorganic material and concentrated to give 17.5 g. crude product. This was chromatographed on a 250 g. magnesium silicate column to give 12.0 g. of fairly pure product (63% yield). Molecular distillation at 250° C. gave 6.7 g. of yellow glass. The oil was dissolved in ether and treated with ethereal hydrogen chloride to give a hydroscopic hydrochloride salt. The salt was triturated in boiling isopropyl ether and was recrystallized from isopropyl ether-chloroform. The salt which as shown by nuclear magnetic resonance and mass spectral analysis to be solvated was dried at 120° C. in a vacuum oven. The salt, m.p. 204°-206° C., analyzed as a ¼ hydrate.

Analysis: Calculated for $C_{27}H_{28}N_2OFCl_2S \cdot 1/4 H_2O$: C, 62.13: H, 5.31; N, 5.37; Found C, 62.04; H, 5.23; N, 5.40.

EXAMPLE 8

2-Bromo-10-[3-(4-p-fluorobenzoylpiperidinyl)propyl] phenothiazine Hydrochloride.

A stirred mixture of 8.86 g. (0.025 mole) of 2-bromo-10-(3-chloropropyl)phenothiazine, 5.18 g. (0.025 mole) of 4-(p-fluorobenzoyl)piperidine and 10 g. of potassium carbonate in 100 ml. of dry dimethylformamide was heated at 90°-100° C. for 24 hours. The cooled reaction mixture was filtered, the dimethylformamide removed at reduced pressure and the residue mixed with dry ether and the ether mixture filtered to remove solids. The dry ether solution was treated with ethereal hydrogen chloride to give the 2-bromo-10-[3-(4-p-fluorobenzoylpiperidinyl)propyl]phenothiazine hydrochloride.

Effective quantities of any of the foregoing pharmacologically active compounds of Formula I may be administered to a living animal body for therapeutic purposes according to usual modes of administration and in usual forms, such as orally in solutions, emulsions, suspensions, tablets and capsules in pharmaceutically acceptable carriers and parenterally in the form of sterile solutions.

For the parenteral administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from two milligrams or above and preferably 5, 10, 25 milligrams or even higher depending, of course, upon the emergency of the situation and the particular result desired. Five to 25 milligrams appears optimum per unit dose. Daily dosages should preferably range from 4 to 100 mg. The active ingredients of the invention may be combined with other pharmacologically active agents as stated above. It is only necessary that the active ingredient constitute an effective amount; i.e., such that a suitable effective dosage will be obtained consistent with the dosage form employed. Obviously, several unit dosage forms may be administered at about the same time.

The following formulations are representative for all of the pharmacologically active compounds of this invention.

FORMULATIONS

1. Capsules

Capsules of 2 mg., 5 mg., 10 mg., and 25 mg. of active ingredient per capsule are prepared. With the higher amounts of active ingredient, reduction may be made in the amount of lactose.

| Typical blend for encapsulation | Per Capsule, mg. |
| --- | --- |
| Active ingredient, as salt | 2 |
| Lactose | 259 |
| Starch | 126 |
| Magnesium stearate | 4 |
| Total | 391 |

| Ingredients | 5 mg. per Capsule | 10 mg. per Capsule | 25 mg. per Capsule |
| --- | --- | --- | --- |
| Active ingredient, as salt | 5 | 10 | 25 |
| Lactose | 250 | 240 | 225 |
| Starch | 126 | 126 | 126 |
| Magnesium stearate | 4 | 6 | 8 |
| Total | 385 | 382 | 384 |

In each case, uniformly blend the selected active ingredient with lactose, starch, and magnesium stearate and encapsulate the blend.

2. A typical formulation for a tablet containing 5.0 mg. of active ingredient per tablet follows. The formulation may be used for other strengths of active ingredient by adjustment of weight of dicalcium phosphate.

|   | Per Tablet. mg. |
| --- | --- |
| 1. Active ingredient | 5.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 202.0 |

Uniformly blend 1, 2, 4 and 5. Prepare 3 as a 10 per cent paste in water. Granulate the blend with starch paste and pass the wet mass through an eight mesh screen. The wet granulation is dried and sized through a twelve mesh screen. The dried granules are blended with the calcium stearate and compressed.

| (3) Injectable - 2% sterile solution | Per cc |
| --- | --- |
| Active ingredient mg. | 20 |
| Preservative, e.g. chlorobutanol, wt./vol. percent | 0.5 |
| Water for injection q.s. |  |

Prepare solution, clarify by filtration, fill into vials, seal and autoclave.

What is claimed is:

1. A compound selected from 10-[ω-(benzoylpiperidinyl)alkyl] phenothiazines having the formula:

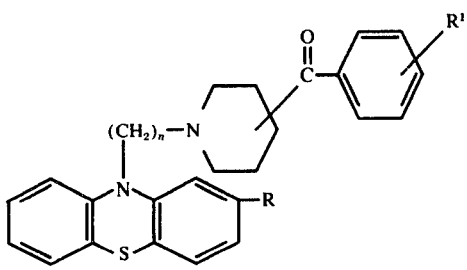

wherein;

R is selected from the group consisting of hydrogen, bromo, chloro, trifluoromethyl, lower alkoxy, acetyl, sulfamoyl, or dimethylsulfamoyl, R¹ is selected from the group consisting of hydrogen, chloro, bromo, fluoro, trifluoromethyl, lower alkoxy, or lower alkyl, n is a positive integer from 2–4 inclusive, and non-toxic pharmaceutically acceptable acid addition salts thereof.

2. A compound selected from 10-[3-(benzoyl-piperidinyl)propyl] phenothiazines having the formula:

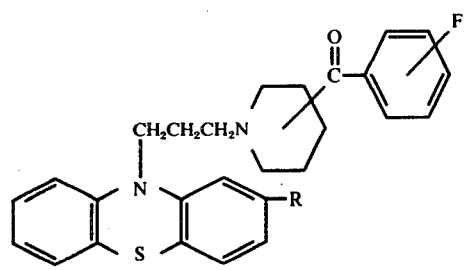

wherein;

R is selected from the group consisting of hydrogen, bromo, chloro, trifluoromethyl, lower alkoxy, acetyl, sulfamoyl or dimethylsulfamoyl, and non-toxic pharamaceutically acceptable acid addition salts thereof.

3. A compound selected from 10-[3-(benzoyl-piperidinyl)propyl] phenothiazines having the formula:

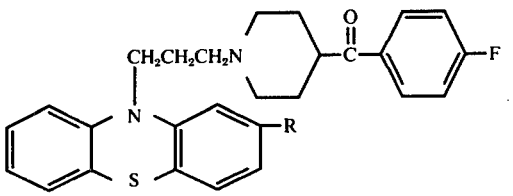

wherein;

R is selected from the group consisting of hydrogen, bromo, chloro, trifluoromethyl, lower alkoxy, acetyl, sulfamoyl or dimethylsulfamoyl, and non-toxic pharmaceutically acceptable acid addition salts thereof.

4. The compound of claim 3 which is 10-{3-[4-(p-fluorobenzoyl)-piperidinyl]propyl}phenothiazine.

5. The compound of claim 3 which is 2-tri-fluoromethyl-10-{3-[4-(p-fluorobenzoyl)piperidinyl]-propyl}phenothiazine.

6. 2-Chloro-10-{3-[4-(p-fluorobenzoyl)piperidinyl]-propyl}phenothiazine.

7. The compound of claim 6 in the form of a non-toxic pharmaceutically acceptable acid addition salt.

8. 2-Acetyl-10-[3-(p-fluorobenzoylpiperidinyl)propyl] phenothiazine.

9. The compound of claim 8 in the form off a non-toxic pharmaceutically acceptable acid addition salt.

10. A pharmaceutical composition useful for its tranquilizing properties comprising (a) an effective amount of a 10-[ω-(benzoylpiperidinyl)alkyl]phenothiazine having the formula:

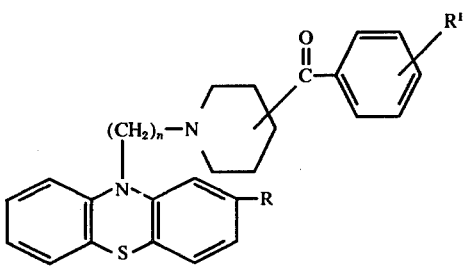

wherein;

R is selected from the group consisting of hydrogen, bromo, chloro, trifluoromethyl, lower alkoxy, acetyl, sulfamoyl or dimethylsulfamoyl, R¹ is selected from the group consisting of hydrogen, chloro, bromo, fluoro, trifluoromethyl, lower alkoxy or lower alkyl, n is a positive integer from 2–4 inclusive, and (b) a pharmaceutically acceptable carrier therefor.

11. A pharmaceutical composition a defined in claim 10, wherein the active ingredient is in the form of a non-toxic pharmaceutically acceptable acid addition salt.

12. A pharmaceutical composition as defined in claim 11, wherein the active ingredient is present in the amount of from 5 to 500 milligrams.

13. The pharmaceutical composition as defined in claim 12, wherein the active ingredient is 2-acetyl-10-{3-[4-(p-fluorobenzoyl) piperidinyl]propyl}phenothiazine.

14. The pharmaceutical compositions as defined in claim 12, wherein the active ingredient is 2-tri-fluoromethyl-10-{3-[4-(p-fluorobenzoyl)piperidinyl]-propyl}phenothiazine.

15. A pharmaceutical composition useful for its tranquilizing properties comprising (a) an effective amount of 2-chloro-10-{3-[4-(p-fluorobenzoyl)piperidinyl]-propyl}phenothiazine or a non-toxic pharmaceutically acceptable acid addition salt thereof and (b) a pharmaceutically acceptable carrier therefor.

16. A method for inducing tranquilization in a mammal comprising administering to a mammal a tranquilizing effective amount of a compound having the formula:

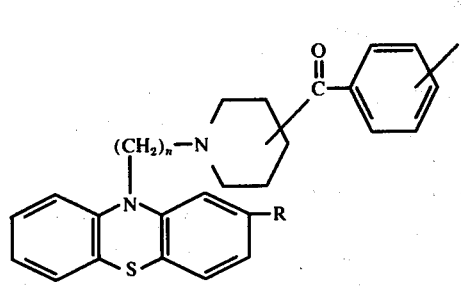

wherein;
R is selected from the group consisting of hydrogen, bromo, chloro, trifluoromethyl, lower alkoxy, acetyl, sulfamoyl or dimethylsulfamoyl,
R¹ is selected from the group consisting of hydrogen, chloro, bromo, fluoro, trifluoromethyl, lower alkoxy or lower alkyl, and
n is a positive integer from 2–4 inclusive.

17. The method according to claim 16 wherein the active ingredient is in the form of a pharmaceutically acceptable acid addition salt.

18. The method according to claim 17 wherein the active ingredient is administered together with a pharmaceutically acceptable carrier therefor and in an amount of about one to 500 milligrams.

19. The method according to claim 18 wherein the active ingredient is 2-acetyl-10-{3-[4-(p-fluorobenzoyl)piperidinyl]propyl}phenothiazine.

20. The method according to claim 18 wherein the active ingredient is 2-trifluoromethyl-10-{3-[4-(p-fluorobenzoyl) piperidinyl]propyl}phenothiazine.

21. A method for inducing tranquilization in a mammal comprising administering to a mammal a tranquilizing effective amount of 2-chloro-10-[3-(4-p-fluorobenzoylpiperidinyl)propyl]phenothiazine or a non-toxic pharmaceutically acceptable acid addition salt thereof.

22. A process for the preparation of 10-[ω-(benzoylpiperidinyl) alkyl]phenothiazines having the formula:

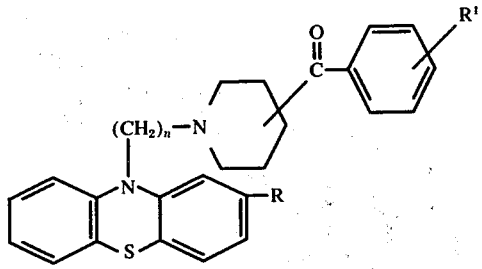

wherein;
R is selected from the group consisting of hydrogen, bromo, chloro, trifluoromethyl, lower alkoxy, acetyl, sulfamoyl or dimethylsulfamoyl,
R¹ is selected from the group consisting of hydrogen, chloro, bromo, fluoro, trifluoromethyl, lower alkoxy or lower alkyl, and
n is a positive integer from 2-4 inclusive, which comprises mixing and heating in an aprotic solvent at a temperature from about 80°–130° C. in the presence of a strong inorganic base a 1-(ω-haloalkyl)-4-(2 or 3)-benzoylpiperidine of the formula:

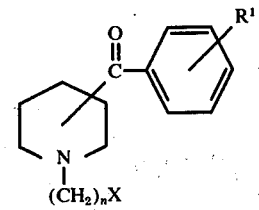

wherein n and R¹ are as defined hereinabove and X is chloro, bromo or iodo with a phenothiazine of the formula:

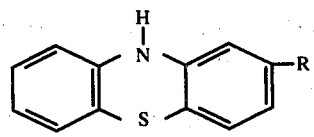

wherein R is as defined hereinabove.

* * * * *

UNITED STATES PATENT AND TRADEMARK OFFICE
CERTIFICATE OF CORRECTION

PATENT NO. : 4,021,552
DATED : May 3, 1977
INVENTOR(S) : William J. Welstead, Jr. and Robert F. Boswell, Jr.

It is certified that error appears in the above-identified patent and that said Letters Patent are hereby corrected as shown below:

In column 2, line 4, "rats" should be changed to read --mice--

Signed and Sealed this

Thirteenth Day of December 1977

[SEAL]

Attest:

RUTH C. MASON
Attesting Officer

LUTRELLE F. PARKER
Acting Commissioner of Patents and Trademarks